US008055487B2

(12) United States Patent
James

(10) Patent No.: US 8,055,487 B2
(45) Date of Patent: Nov. 8, 2011

(54) INTERACTIVE ORTHOPAEDIC BIOMECHANICS SYSTEM

(75) Inventor: Anthony James, Bartlett, TN (US)

(73) Assignee: Smith & Nephew, Inc., Memphis, TN (US)

( * ) Notice: Subject to any disclaimer, the term of this patent is extended or adjusted under 35 U.S.C. 154(b) by 1051 days.

(21) Appl. No.: 11/359,255

(22) Filed: Feb. 22, 2006

(65) Prior Publication Data

US 2006/0195198 A1 Aug. 31, 2006

Related U.S. Application Data

(60) Provisional application No. 60/655,131, filed on Feb. 22, 2005.

(51) Int. Cl.
*G06G 7/48* (2006.01)
(52) U.S. Cl. .............. 703/6; 703/11; 434/262; 434/270; 434/265
(58) Field of Classification Search .................... 606/89, 606/53; 424/423; 600/407, 443; 700/118
See application file for complete search history.

(56) References Cited

U.S. PATENT DOCUMENTS

| | | | |
|---|---|---|---|
| 5,180,380 A | 1/1993 | Pursley et al. | |
| 5,632,748 A * | 5/1997 | Beck et al. ................ | 606/89 |
| 5,702,389 A | 12/1997 | Taylor et al. | |
| 5,728,095 A | 3/1998 | Taylor et al. | |
| 5,871,018 A | 2/1999 | Delp et al. | |
| 5,891,143 A | 4/1999 | Taylor et al. | |
| 5,971,984 A | 10/1999 | Taylor et al. | |
| 6,002,859 A | 12/1999 | DiGioia, III et al. | |
| 6,030,386 A | 2/2000 | Taylor et al. | |
| 6,129,727 A | 10/2000 | Austin et al. | |
| 6,205,411 B1 | 3/2001 | DiGioia, III et al. | |
| 6,236,878 B1 | 5/2001 | Taylor et al. | |
| 6,301,495 B1 | 10/2001 | Gueziec et al. | |
| 6,533,737 B1 | 3/2003 | Brosseau et al. | |
| 6,697,664 B2 | 2/2004 | Kienzie, III et al. | |
| 6,701,174 B1 | 3/2004 | Krause et al. | |
| 6,711,432 B1 | 3/2004 | Krause et al. | |
| 6,917,827 B2 | 7/2005 | Kienzie, III | |
| 6,922,581 B2 | 7/2005 | Kienzie, III | |

(Continued)

FOREIGN PATENT DOCUMENTS

| | | |
|---|---|---|
| FR | 2576774 | 8/1996 |
| WO | WO 98/04203 A2 | 2/1998 |
| WO | WO 02/37935 A2 | 5/2002 |

OTHER PUBLICATIONS

Ignace Naert, Joke Duyck, Hans Jacob Ronold, Hans Van Ooterwyck, Jos Vander Sloten, Jan Eirik Ellingsen The influence of static and dynamic loading on marginal bone reactions around ossoeointegrated implants: an animal experimental study ISSN 0905-7161, Clin. Oral Impl. Res. 12, 2001, pp. 207-218.*

(Continued)

*Primary Examiner* — Kamini S Shah
*Assistant Examiner* — Cuong Luu
(74) *Attorney, Agent, or Firm* — Fish & Richardson P.C.

(57) ABSTRACT

Methods of selecting a configuration of fixation and compression screws for a bone plate to be installed on a bone of a patient. A computer or website allows a user to load images of a fractured bone and specify a particular configuration of fixation and compression screws with a plate on the loaded bone. The computer replicates stresses imposed on the bone by regular activities using finite element analysis and provide information about the suitability of the selected configuration.

27 Claims, 5 Drawing Sheets

U.S. PATENT DOCUMENTS

| | | | |
|---|---|---|---|
| 6,947,783 | B2 | 9/2005 | Immerz |
| 6,978,188 | B1 * | 12/2005 | Christensen .................. 700/118 |
| 7,507,253 | B2 * | 3/2009 | Nordquist .................. 623/16.11 |
| 2001/0036245 | A1 | 11/2001 | Kienzle, III et al. |
| 2002/0010465 | A1 | 1/2002 | Koo et al. |
| 2002/0038085 | A1 | 3/2002 | Immerz |
| 2002/0107522 | A1 | 8/2002 | Picard et al. |
| 2003/0120347 | A1 | 6/2003 | Steinberg |
| 2003/0191466 | A1 | 10/2003 | Austin et al. |
| 2004/0009459 | A1 | 1/2004 | Anderson et al. |
| 2004/0039259 | A1 | 2/2004 | Krause et al. |
| 2004/0059331 | A1 | 3/2004 | Mullaney |
| 2004/0068187 | A1 * | 4/2004 | Krause et al. .................. 600/443 |
| 2004/0073211 | A1 | 4/2004 | Austin et al. |
| 2004/0073228 | A1 | 4/2004 | Kienzle et al. |
| 2004/0078212 | A1 | 4/2004 | Anderson et al. |
| 2004/0097922 | A1 | 5/2004 | Mullaney |
| 2004/0171924 | A1 | 9/2004 | Mire et al. |
| 2004/0240715 | A1 | 12/2004 | Wicker et al. |
| 2005/0010106 | A1 | 1/2005 | Lang et al. |
| 2005/0059873 | A1 * | 3/2005 | Glozman et al. .............. 600/407 |
| 2005/0081161 | A1 * | 4/2005 | MacInnes et al. ............. 715/765 |
| 2005/0090900 | A1 * | 4/2005 | Nordquist .................. 623/17.11 |
| 2005/0208095 | A1 * | 9/2005 | Hunter et al. .................. 424/423 |
| 2005/0209598 | A1 | 9/2005 | Grimm et al. |
| 2005/0209605 | A1 | 9/2005 | Grimm et al. |
| 2007/0173815 | A1 * | 7/2007 | Murase .......................... 606/53 |

OTHER PUBLICATIONS

J. M. Garcia, M. Doblare, J. Cegonino Bone remodeling simulation: a tool for implant design Computational Materials Science 25, 2002, pp. 100-114.*

A. Gefan Optimizing the biomechanical compatibility of orthopedic screws for bone fracture fixation Medical Engineering & Physics 24, 2002, pp. 337-347.*

Google images of Liss Plates.*

Google images of Locking Plates.*

E. Erkmen, B. Simsek, E. Yucel, A. Kurt Comparison of Different Fixation Methods Following Sagittal Split Ramus Osteotomies Using Three-dimensional Finite Elements Analysis Part 1: Advancement Surgery—Posterior Loading, Int. J. Oral Maxillofac. Surg. 2005; 34; pp. 551-558.*

Google images of Liss Plates, Jan. 2010.*

Google images of Locking Plates, Jan. 2010.*

Bonecraft LLC "Innovation Works" website page and five pages of photographs (May 30, 2001).

Croitoru, et al., Clinical Paper entitled "Fixation-Based Surgery : A New Technique for Distal Radius Osteotomy," *Computer Aided Surgery*, 6:160-169 (2001).

Paper entitled "Planning and Performing the Ilizarov Method with the Taylor Spatial Frame," by Iyun, et al., pp. 145-147 (date unknown).

Distraction The Newsletter of ASAMI-North America, "Taylor Spatial Frame Disorients Ilizarovians," Green, S., vol. 5, No. 1, Jan. 1997, pp. 1-9, XP002137410, p. 5.

'Expedited Finite Element Analysis of Ankle External Fixation Stiffness' by Jonathan Kirk Nielsen, A thesis submitted in partial fulfillment of the requirements for the Master of Science degree in Biomedical Engineering in the Graduate College of The University of Iowa, 77 pages (Jul. 2004).

International Search Report and Written Opinion in related Application No. PCT/US07/18260.

* cited by examiner

INTERACTIVE ORTHOPAEDIC BIOMECHANICS SYSTEM

RELATED APPLICATION

The present application claims the benefit of provisional patent application Ser. No. 60/655,131 filed on Feb. 22, 2005 entitled "Interactive Orthopaedic Biomechanics System," the contents of which are incorporated herein by reference.

FIELD OF THE INVENTION

The present invention relates generally to biomechanical and other medical studies. More specifically, the present invention relates to computer systems that provide information on, simulate, and/or model possible permutations of fracture types and medical device constructs.

BACKGROUND

Bone fractures, deformities and other conditions may be treated using a variety of medical devices. A surgeon selecting an appropriate medical device or devices for treatment of a fracture may take into account information about the fracture, the potential devices, the individual patient, and/or the potential stresses and motions to which the bone and device may be subject, among other things. In the case of plates used to treat bone fractures, in order to treat a fracture appropriately, surgeons and others desire to know or predict the proper plate/screw configuration to optimize the biomechanics of the particular fracture they are treating. They also frequently need to select between locking and traditional non-locked screws, which may perform in significantly different ways because of biomechanic differences. In short, selection of an appropriate medical device may be limited by a surgeon's limited ability to predict the performance of potential fracture and medical device constructs.

Various studies are underway to evaluate the plate/bone biomechanics of common fractures. However, there are many challenges in dealing with the many permutations of fracture, plate, and locked or unlocked screws. Biomechanics studies defining the biomechanics for a particular fracture/plate construct typically provide information only for the particular fracture/plate constructs and do not provide any ability to evaluate or optimize among multiple permutations of fracture type and constructs. Often surgeons do not have information about the specific biomechanics of the patients they are treating and simply rely on instinct and experience to select among alternative options.

The July 2004 thesis of Jonathan Kirk Nielson titled "Expedited Finite Element Analysis of Ankle External Fixation Stiffness," which is incorporated herein by this reference, discloses software for measuring Ilizarov distal tibia frame axial stiffness that utilizes finite element analysis software. The software allows a user to specify different wire and pin configurations as input and delivers axial movement of the tibia as output. However, the approach does not include the actual bone or fracture(s) in the bone in the characterization.

There is a need for enhanced simulation capabilities and, in the context of plate devices, there is a need for simulation of performance of alternative plate/screw configurations that takes into account actual bone, plate type, and/or screw configuration characteristics. Such simulation may allow selection of among alternative configurations to optimize biomechanics and provide more rapid healing, fewer non-unions and failures. There is a further need for a computer system that offers adequate simulation that allows a surgeon to input information about the fracture type and characteristics, as well as potential plate and screw combinations, and choose the appropriate plate and locked or unlocked screw configuration to optimize the biomechanics for the fracture and other bone characteristics of the patient. Similar needs also exist for other types of devices, including, but not limited to, screws, external fixators and other devices used in orthopaedic or trauma applications.

SUMMARY

One embodiment of the present invention provides a method of selecting a bone, plate, and configuration of fixation and compression screws for the bone plate to be installed on a bone of a patient. The method involves inputting into a computer, having a processor, memory and input/output functionality, information about one or more of (1) the bone; (2) the patient; (3) static and dynamic physical forces to which the bone will be subjected; (4) a candidate bone plate; and (5) fixation and compression screws adapted to be potentially used with the plate. The method also involves simulating in the computer (1) the bone plate secured to the bone using a first configuration of fixation and compression screws, and (2) performance of the structure comprising the bone plate, bone and the first configuration of the fixation and compression screws. The method further involves simulating in the computer (1) the bone plate secured to the bone using a second configuration of fixation and compression screws, and (2) performance of the structure comprising the bone plate, bone and the second configuration of the fixation and compression screws. The method further involves selecting a selected configuration of fixation and compression screws based on these simulations.

In certain embodiments, the method may involve using finite element analysis for simulating performance of the structure comprising the bone plate, bone, and first configuration of the fixation and compression screws and/or simulating performance of the structure comprising the bone plate, bone, and second configuration of the fixation and compression screws. Other embodiments involve providing the selected configuration to a user over the world wide web. Yet other embodiments involve each screw configuration having, for each aperture in the locking plate, either a non-locking screw, a locking screw, or no screw. In yet other embodiments, the method may further involve providing an interface for a remote user to input constraints for the simulation over the Internet, and/or providing the selected configuration to the remote user.

Another embodiment of the invention involves a method for using a computer to evaluate one or more options for associating at least one surgical device with a bone. A standard computer may be used and will typically include processing functionality, memory functionality, input functionality and output functionality. The computer accepts a plurality of information elements as input. An information element may be any piece of information or data that is stored in any suitable data format, e.g., in a database record, a file, a message, etc. The method involves (a) inputting at least one first information element into the computer concerning the bone, (b) inputting at least one second information element into the computer concerning the surgical device, (c) inputting at least one third information element into the computer concerning a scenario for associating the surgical device with the bone, (d) using the computer, analyzing the first, second and third information elements, (e) using the computer, outputting at least one fourth information element predicting at least one performance characteristic of the scenario, and (f)

using the fourth information element to evaluate whether to follow the scenario to associate the surgical device with the bone or to otherwise evaluate and/or record the biomechanical construct. The first information element may further concern a fracture in the bone, information about the fracture that is rendered on a computer image of a bone, the side of the bone the fracture is on, the type of fracture, and/or the bone condition, among other things. The second information element may further concern the type of the device, the position of the device, information about the selection of at least one screw for use in a hole in the device, and/or information about the characteristics of a screw for use in a hole in the device. Inputting the second information element may further comprise displaying a plurality of holes on a graphical image of the device affixed to the bone and selecting a hole on the image of the device for a screw. The method may further involve optimizing screw configuration by running iterations to minimize one or more of stress and motion.

In some embodiments, one or more of the information elements may be inputted using interactive screens or menus displayed by the computing device. The data for input may be gathered in any suitable or desirable manner, including, but not limited to, digital or non-digital x-ray technology, fluoroscopy technology, computer assisted surgical navigation technology, measuring devices, databases, kinetic evaluation, or other types of evaluation. In some embodiments, the computer may communicate with the device or systems used to gather the data, eliminating the need for the user to input the data. Rather, the systems may, in some embodiments, automatically enter or input the data.

The invention may involve a variety of types and configurations of surgical devices providing conventional, non-conventional, and/or a combination of conventional and non-conventional fixation means including plates, screws, pegs, nails, external fixators, bioresorbably fixation elements, bone glue, etc. In certain embodiments, a surgeon can use the invention to evaluate which size hip or knee implant optimizes the biomechanics. This is frequently a combination of the amount of bone to take out versus the size of implant to use. For example, in some situations, it may be prudent to remove more bone to get a larger implant in place, yielding a better transfer of load to the bone. In other cases, it may be better to preserve bone and use a smaller implant. This could apply to hip femoral components, knee femoral and tibia components, acetabulum components, etc.

Additional features, objects, and advantages of the invention will become apparent from the drawings and the detailed description of the preferred embodiments.

DETAILED DESCRIPTION

Figure 1:
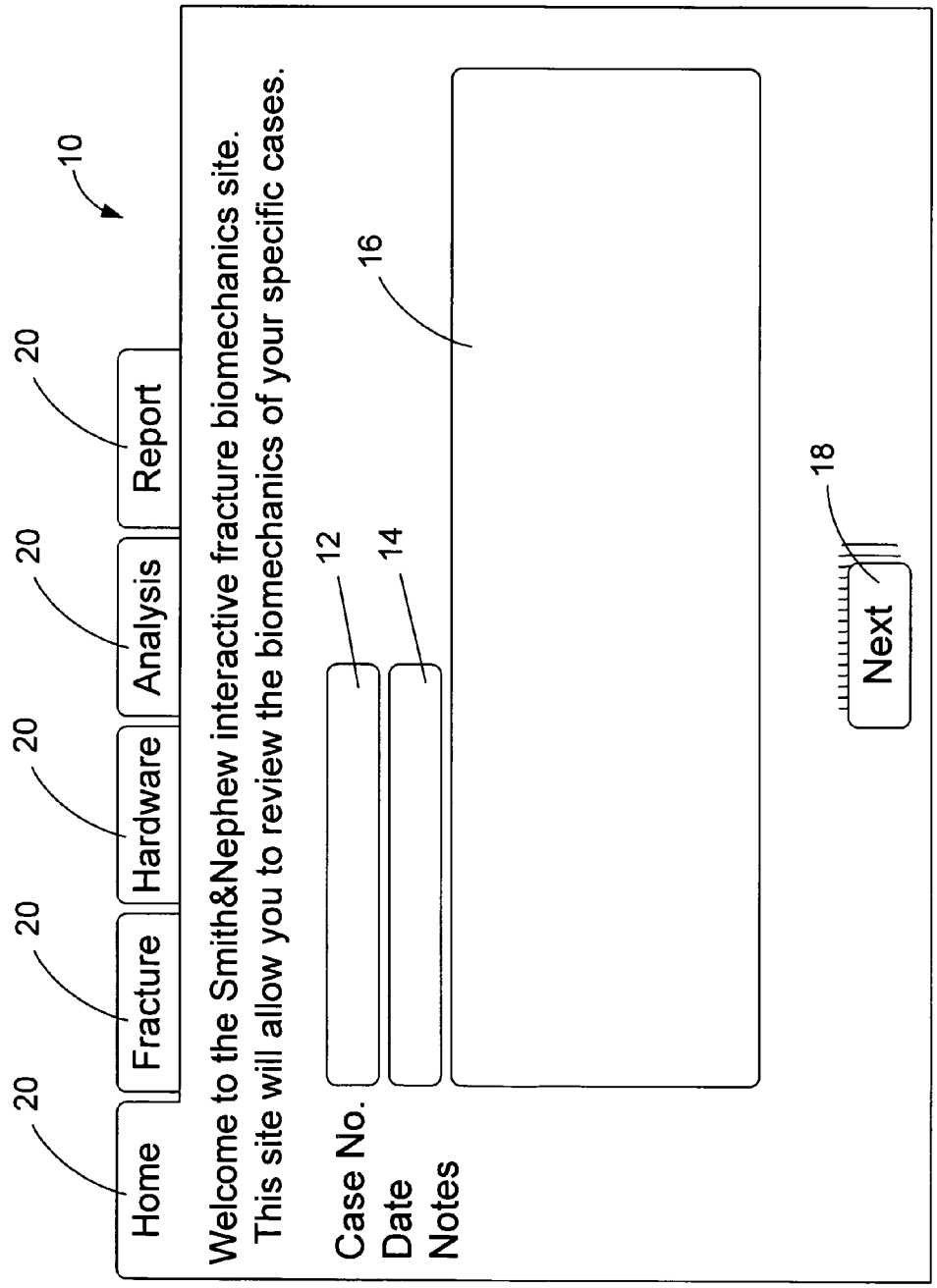
FIG. 1 illustrates a computer interface for inputting and displaying information about a case, according to an embodiment of the invention.

One embodiment of the present invention provides a computer or website that allows a user to load images of a fractured bone and specify a particular configuration of fixation and compression screws with a plate on the loaded bone. The computer is able to replicate normal stresses imposed on the bone by regular activities using finite element analysis. The loaded images may originate from radiographs of the actual fractured bone or may be a predefined bone structure already stored. In one embodiment, the computer is also able to predict which combination of screws will work best. This approach can be applied to any bone/device construct including nails, external fixators, and other products. Also, this system can be developed as a web based system using advanced software analysis tools or as a stand alone system that is programmed for the specific application.

In certain embodiments, the system allows a surgeon or other person to access a website and input information about a patient's fracture and the plate, or other device being considered. The surgeon or other user may also input information about the particular patient, such as age, weight, height, etc., and/or information about the expected loads or stresses to which the bone may be subjected. Using the inputted information elements, the system performs one or more of a variety of mechanical and biomechanical analysis and returns information to the surgeon or other user that may be used to optimize or otherwise enhance patient treatment.

The analysis may utilize specific information about the patient or may use normal, average, or other appropriate data when patient specific data is not provided or otherwise cannot be used. This approach can be applied to any bone/device construct including nails, external fixators, and other products. Also, this system can be developed as a web based system using advanced software analysis tools or as a stand alone system that is programmed for the specific application. The system may utilize prior laboratory results regarding the performance of possible bone/device constructs. For example, in the case of bone plates, by performing laboratory biomechanical studies, various fracture/plate constructs can be evaluated. Based on this information, a computer simulation model can be developed that correlates and defines all the possible permutations of fracture type and plate construct. Such simulations can provide surgeons and other users valuable information about potential failure points and stress distribution for various medical device configurations being considered. In addition to simulations, systems according to the present invention can provide reference information, such as database information about common fracture types and bone conditions and statistics about medical device configurations used to treat fracture types and bone conditions. Such information can also aid the surgeon or other user in selecting an appropriate means for treating a patient's bone condition.

FIGS. 1-5 illustrate an exemplary computer interface for a simulation system according to certain embodiments of the present invention. The computer simulation may utilize a finite element analysis of the bone/plate construct that shows the surgeon how to optimize the construct for the appropriate stiffness and stress. A standard computer may be used and will typically include processing functionality, memory functionality, input functionality and output functionality. The system may utilize a variety of software and network components to provide a user interface, remote access, shared access, and to perform and report any analysis.

In FIGS. 1-5, a software program provides the exemplary computer interface for a simulation system according to certain embodiments of the present invention. FIG. 1 illustrates a computer user interface 10 for inputting and displaying information about a patient case. The user interface 10 allows a surgeon or other user to enter a case number 12, a date 14, and notes 16. Other information may be entered about the case, such as planned surgery date, surgeon name, surgeon contact information, as well as any other suitable or appropriate information. A next button 18 allows a surgeon or other user to proceed or continue to further interface screens such as the screen of FIG. 2. A series of tabs 20 also allows navigation to other portions of the user interface associated with the case.

Figure 2:
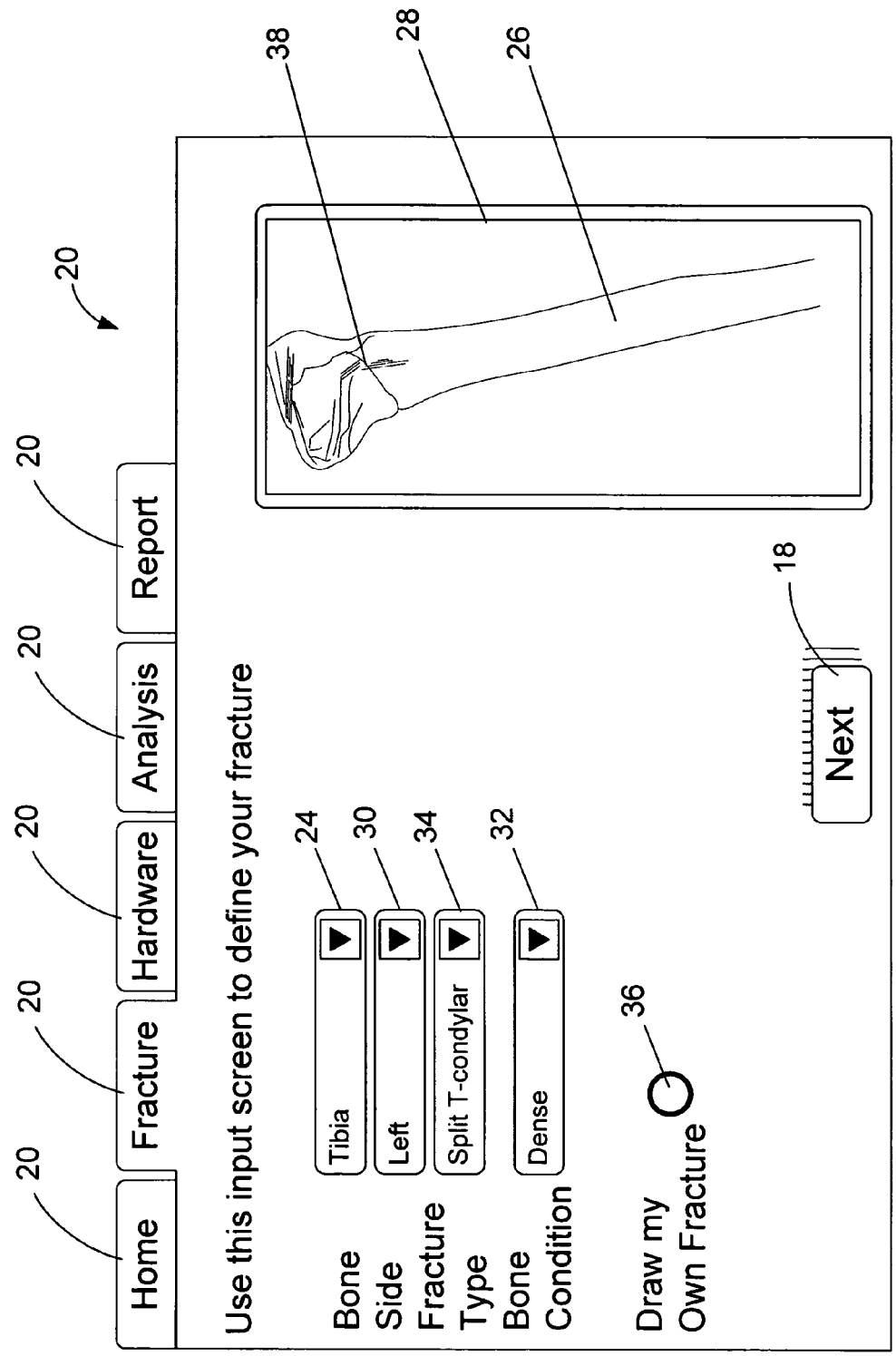
FIG. 2 illustrates a computer interface for inputting and displaying information about a bone and/or fracture, according to an embodiment of the invention.

FIG. 2 illustrates a computer interface 22 for inputting and displaying information about a bone and/or fracture. In certain embodiments, the computer interface will display an image of a bone. For example, as illustrated in FIG. 2, the interface may allow a surgeon or other user to input a bone (e.g., femur, tibia, fibula, calcaneous, humerus, etc.), in a bone field 24. Upon identification of a bone, the computer interface 22, may display an image of that bone, or a portion of that bone. For example, in FIG. 2, upon selection of "tibia," a tibia 26 may be displayed in a window 28 of the interface 22. The interface 22 may also allow a surgeon or other user to specify a side 30. Such selection may also be reflected in the image of the bone 26 (i.e., the image may show the left side of the bone, or the proximal end of the bone, etc.).

The interface 22 may also allow a surgeon to input an image of a bone from another source. For example, the user may identify a photograph, scan, x-ray, digital image, or other type of image of the patient's own bone. Alternatively, the mechanical axis and/or bone landmarks may be inputted by the user (or identified using pattern recognition functionality or the like) to be used as information elements in the simulation. The software may recognize and model the bone based on the scanned image to create data for the simulation. The interface may also offer pictures or other images of bones from which the surgeon or other user may select. For example, after a user has identified a "tibia," the interface may provide images of various tibias that have been laboratory tested. Thus, the system can give users several combinations for various "standard" configurations of fractures for the surgeon to use as a benchmark at least. Upon selection of a "tibia" image that most closely or appropriately resembles or represents the patient's tibia, the software may update the image of the tibia 26 on the interface 22 and use one or more information elements regarding the specific tibia inputted or otherwise selected in a simulation or modeling that is ultimately executed.

In FIG. 2, the interface allows a surgeon or other user to input a bone condition 32. In certain embodiments, the surgeon or other user may input additional information about the bone that allows the software to more accurately model the bone. For example, the surgeon or other user may specify specific bone dimension, perhaps measured on an x-ray. Entry of additional information about the bone may allow the software to more accurately display and model the bone/fracture/device combination that is being evaluated.

In the interface 22 shown in FIG. 2, the surgeon or other user also has the ability to select a fracture type 34 or "Draw my Own Fracture" 36. Upon selection of a fracture type 34, in certain embodiments, the interface 22 will display a fracture 38 of that type ("Split T-condylar") on the image of the bone 26, displayed in window 28. The surgeon or other user may manually move or, instead, draw the fracture by selecting "Draw my Own Fracture" 36. For example, the user may use a computer mouse to draw the fracture by clicking the mouse button and moving the mouse-controlled curser over the location of the fracture line in the bone image 26. The software may use this drawn-in representation of a fracture to associate or otherwise determine an associated fracture type from a plurality of known fracture types. Alternatively, the software may use the drawn-in fracture to predict a three dimensional fracture through the bone, and use this custom-defined fracture in simulations and displays. Such prediction can utilize any suitable technique, including those that account for bone density, bone type, and other bone characteristics to predict the internal location of a fracture from a drawn-in fracture on a two-dimensional image of the fracture. As yet another alternative, the software may require the surgeon to draw in a fracture on the bone from a variety of perspectives (e.g., ML, AP, etc.) such that these indications can be combined to determine an estimated path of the fracture through the interior of the bone. The software may present the user with a three dimensional image of a fracture and ask the user to confirm that the three dimensional image of the fracture adequately represents the patient's actual fracture. In still another embodiment, two or three dimensional images of the fracture may be inputted into the computer.

Figure 3:
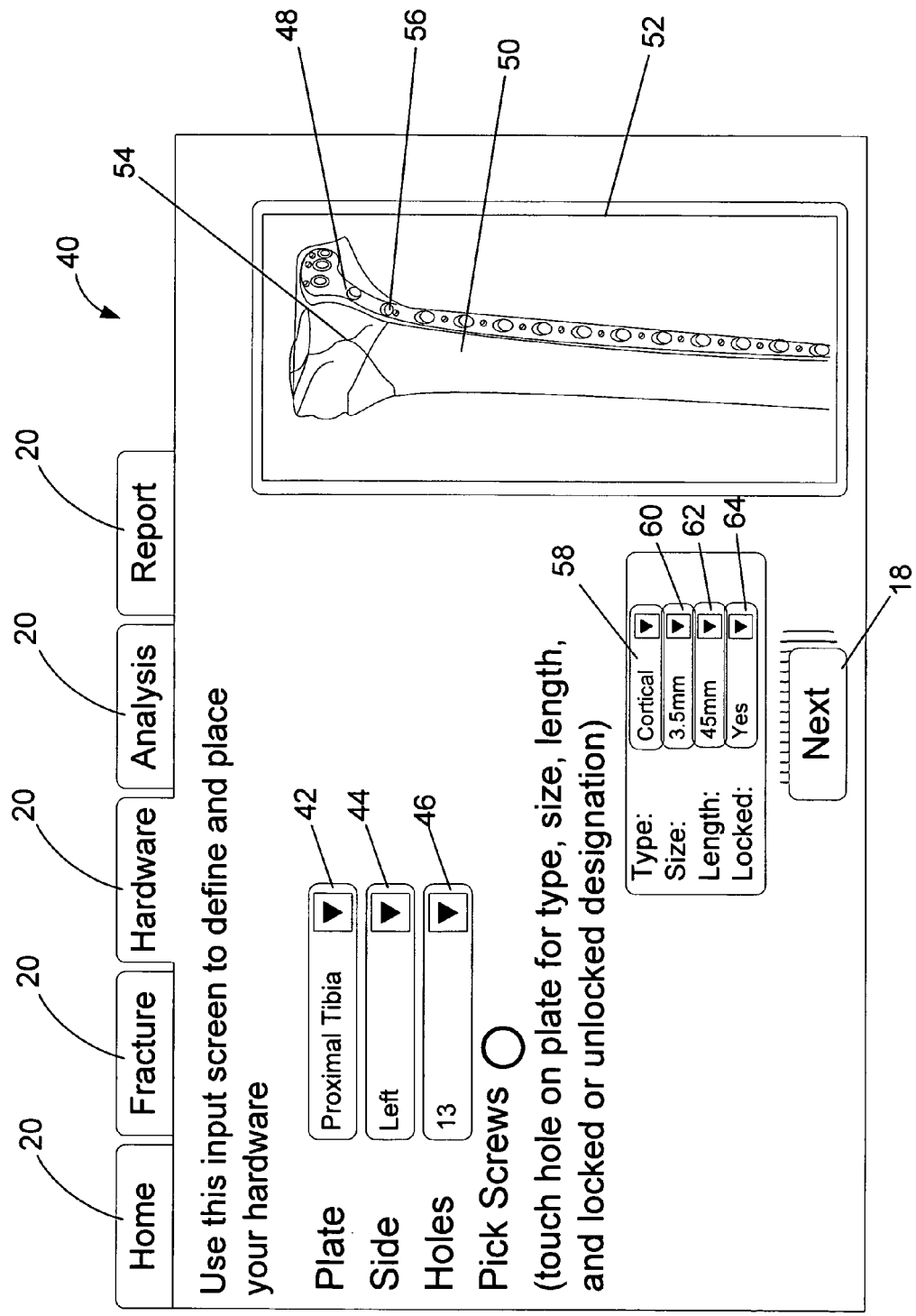
FIG. 3 illustrates a computer interface for inputting and displaying information about an device, bone, and/or fracture, according to an embodiment of the invention.

FIG. 3 illustrates a computer interface 40 for inputting and displaying information about an device, bone, and/or fracture. In this exemplary embodiment, the surgeon or other user may input a plate type 42 (e.g., "Proximal Tibia"), a side 44 (e.g., "Left"), and the number of screw holes in a device 46, among other things. In certain embodiments, the plate, implant, fixator, nail or other medical device is specified allowing a surgeon to evaluate and compare different categories of medical devices (e.g., internal implants, external fixators, bone plates, and intramedullary nails).

In FIG. 3, upon selection of a plate type, a plate of that type 48 is displayed on the image of the bone 50 in the interface image window 52. The fracture 52 may also be displayed. The surgeon or user may have the option to move the position of the plate 48 relative to the bone 50. For example, a user could use the computer mouse by moving the mouse-controlled curser over the plate 48, clicking the mouse button, moving the mouse to move the plate 48, and releasing the mouse once the plate 48 appears in a desired location with respect to the bone 50 displayed on the interface image window 52.

The interface 40 provides users with the option of choosing their own screws by touching or otherwise graphically pointing to one or more of the holes on the plate image 48. For example, a user may move the mouse-controlled curser over the location of a hole 56 in plate 48 and click the mouse button to select a particular hole 56 in the plate 48. Upon this selection, the interface 40 may prompt the user with additional input options, such as the type 58 (e.g., "Cortical"), size 60 (e.g., "3.5 mm"), length 62 (e.g. "45 mm"), and whether or not the instrument is locked or not 64 (e.g. "Yes"). The user may thus select whether or not a hole will have an instrument and thereby select a plate configuration in which one or more of the holes will use either a fixation screw, a compression screw, or some other instrument.

Accordingly, in certain embodiments, a surgeon or other user may select a medical device (e.g., plate, nail, etc.), select a configuration of instruments for use in one or more holes of the device (e.g., which holes will have screws), and select the characteristics of such instruments (e.g., size, length, type, etc.), to establish a potential construct for treatment of a patient.

Figure 4:
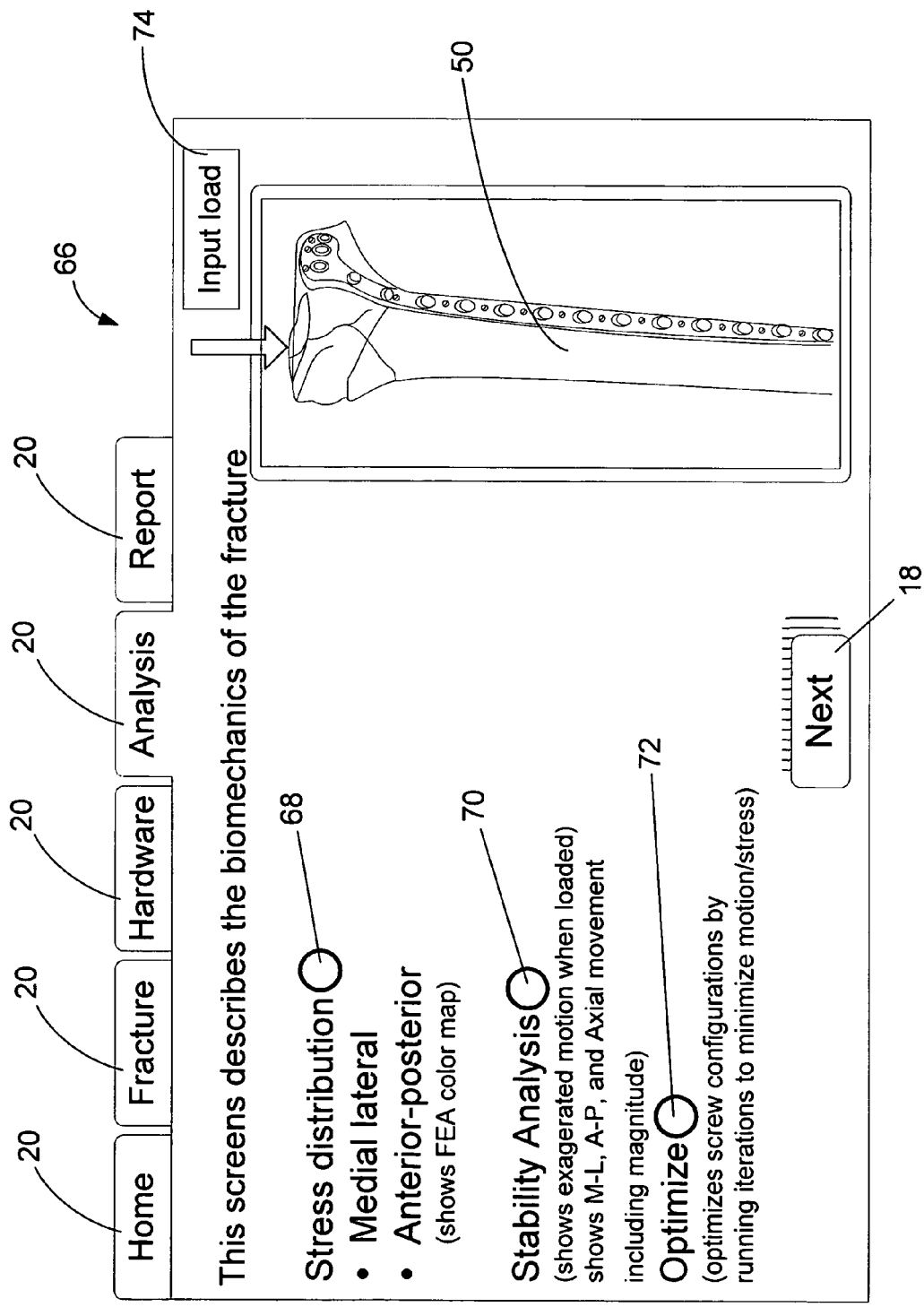
FIG. 4 illustrates a computer interface for selecting analysis of stress distribution, stability, and/or optimization, according to an embodiment of the invention.

FIG. 4 illustrates a computer interface 66 for selecting analysis of stress distribution 68, stability 70, and/or optimization 72. This interface 66 allows a user to specify one or more analysis outputs 68, 70, 72. The stress distribution output selection 68 provides an analysis that simulates and illustrates the stress distribution for the particular bone/instrument construct when a given input load 74 is applied. Such stresses can be imposed statically and/or dynamically, including over repeated cycles to predict failure of the plate and screw combination and/or bone. It may show a finite element analysis color map. The stability analysis output selection 70 provides similar information but for exaggerated motion when loaded. It may show ML, AP, and axial movement including magnitude. The optimize selection option 72 optimizes screw configuration by running iterations to minimize motion and/or stress. Accordingly, the outputs of certain embodiments include finite element analysis color maps showing stress distributions using scale of stresses, motion analysis showing exaggerated movement of construct, flags of high stress or high motion areas, and recommended changes in screw configurations to optimize fracture biomechanics. Stability stiffness of fracture/plate construct in both bending planes, torsion, and axial directions may also be provided. In addition, the output may show where high stress regions are located on the plate and thus indicate trouble spots or possible failure modes. In certain embodiments, a computer interface will also allow a surgeon or other user to input stress conditions to further customize the results of the simulation.

Figure 5:
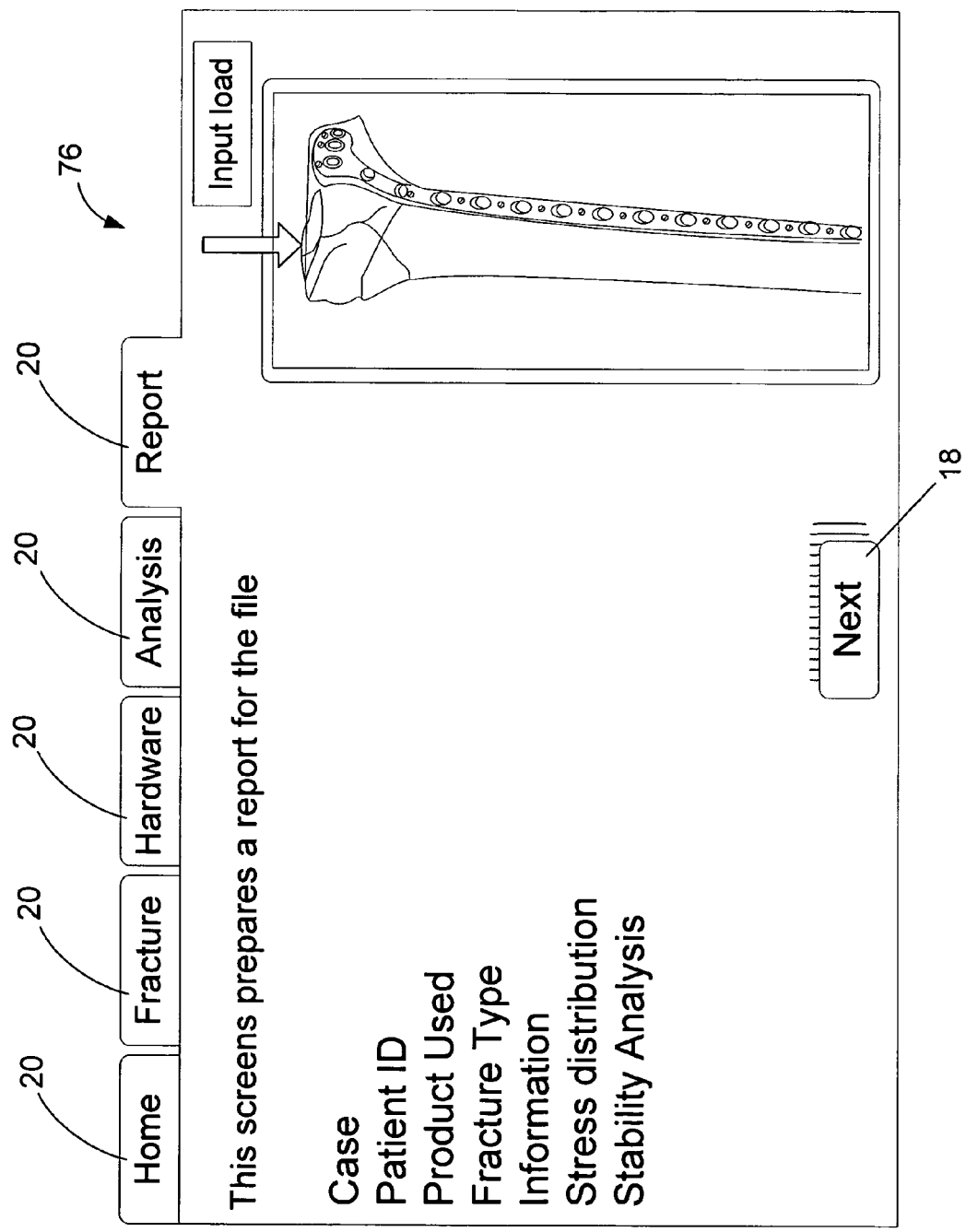
FIG. 5 illustrates a computer interface for displaying a report, according to an embodiment of the invention.

FIG. 5 illustrates a computer interface 76 for displaying a report that summarizes information inputted and displayed in the interfaces of FIGS. 1-4. The results of any analysis selected may also be displayed through this interface. The tabs 20 further allow a user to go back and change inputs in any of the interfaces of FIGS. 1-4 and re-execute the analysis for alternative bone/fracture/instrument constructs.

The interface and software of the present invention may include programming tools as well as Computer Aided Design and analysis software, finite element modeling software, and motion analysis software. In certain embodiments, bone and plate models may be preloaded into the system so that as the surgeon defines the construct, the models would be pulled from a database and shown by a viewer. The software tools would take the inputs listed and produce output that would help the surgeon configure the device to optimize the biomechanics of the fracture.

The foregoing discloses certain embodiments of the present invention, and numerous modifications or alterations may be made without departing from the spirit and the scope of the invention. For example, this invention can be applied to any bone/device construct including nails, external fixators, and other products. Also, this system can be developed as a web based system using advanced software analysis tools or as a stand alone system that is programmed for the specific application.

What is claimed is:

1. A method of selecting a configuration of screws for securing a bone plate to a bone of a patient, comprising:
inputting into a computer, having a processor, memory and input/output functionality, information about one or more of (1) the bone; (2) the patient; (3) physical forces to which the bone will be subjected; (4) a candidate bone plate; or (5) candidate screws adapted to be potentially used with the bone plate;
simulating, in the computer, a performance of a first structure comprising the bone plate, the bone, and a first configuration of screws securing the bone plate to the bone;
simulating, in the computer, a performance of a second structure comprising the bone plate and the bone of the first structure, and a second configuration of screws securing the bone plate to the bone of the first structure, the second configuration being different than the first configuration; and
selecting one of the different configurations of screws based on the simulation of the performance of the first and second structures.

2. The method of claim 1, wherein finite element analysis is used in simulating the two or more different configuration of screws.

3. The method of claim 1 further comprising providing the selected configuration to a user over the world wide web.

4. The method of claim 1, wherein each screw configuration has, for each aperture in the bone plate, either a non-locking screw, a locking screw, or no screw.

5. The method of claim 1 further comprising:
providing an interface for a remote user to input constraints for the simulation over the Internet; and
providing the selected configuration to the remote user.

6. The method of claim 1, wherein the physical forces to which the bone will be subjected comprise static and dynamic forces.

7. The method of claim 1, wherein the physical forces to which the bone will be subjected comprise static forces only.

8. The method of claim 1 further comprising selecting the selected configuration based at least in part on which configuration produces optimum biomechanics.

9. The method of claim 1 further comprising selecting the selected configuration based at least in part on which configuration produces the best stress distribution for healing the bone.

10. A method for using a computer to evaluate options for associating a bone plate with at least one bone, the computer comprising processing functionality, memory functionality, input functionality and output functionality, the method comprising:
(a) inputting at least one first information element into the computer concerning the bone;
(b) inputting at least one second information element into the computer concerning the bone plate and two different configurations of fixation screws and compression screws for use in holes in the bone plate to secure the bone plate to the bone;
(c) inputting at least one third information element into the computer concerning associating the bone plate with the bone;
(d) using the computer, analyzing the first, second and third information elements, wherein analyzing comprises simulating a performance of a first scenario comprising the bone plate, the bone, and one of the two configurations of fixation screws and compression screws and simulating a performance of a second scenario comprising the bone plate and the bone of the first scenario, and the other of the two configurations of fixation screws and compression screws;
(e) using the computer, outputting at least one fourth information element predicting at least one performance characteristic of the first and second scenario; and
(f) using the fourth information element to evaluate the first and second scenario and select one of the two configurations of fixation screws and compression screws based on the evaluation.

11. The method of claim 10, wherein the first information element further concerns a fracture in the bone.

12. The method of claim 11, wherein the first information element further concerns information about the fracture that is drawn on a computer image of a bone.

13. The method of claim 12, wherein the first information element further concerns the side of the bone the fracture is on.

14. The method of claim 12, wherein the first information element further concerns the type of fracture.

15. The method of claim 12, wherein the first information element further concerns the bone condition.

16. The method of claim 11, wherein the second information element further concerns the type of the bone plate.

17. The method of claim 11, wherein the second information element further concerns the position of the bone plate.

18. The method of claim 11, wherein the second information element further concerns information about the selection of at least one screw for use in a hole in the device.

19. The method of claim 11, wherein inputting the second information element comprising displaying a plurality of holes on a graphical image of the device affixed to the bone and selecting a hole on the image of the device for a screw.

20. The method of claim 11, wherein the second information element further concerns information about the characteristics of a screw for use in a hole in the device.

21. The method of claim 11, wherein the third information element further concerns a stress distribution on the bone.

22. The method of claim 11, wherein the third information element further concerns a stability analysis on the bone.

23. The method of claim 11 further comprising optimizing screw configuration by running iterations for different screw configurations to identify a screw configuration that minimizes stress.

24. The method of claim 11 further comprising optimizing screw configuration by running iterations for different screw configurations to identify a screw configuration that minimizes motion.

25. A method of selecting a configuration of fixation screws and compression screws for a bone plate to be installed on a bone of a patient, the method comprising:

inputting into a computer, having a processor, memory and input/output functionality, information about one or more of (1) the bone; (2) the patient; (3) physical forces to which the bone will be subjected; (4) a candidate bone plate; and (5) candidate fixation screws and compression screws adapted to be potentially used with the bone plate;

simulating, in the computer, a performance of a first structure comprising the bone plate, the bone, and a first configuration of fixation screws and compression screws securing the bone plate to the bone;

simulating, in the computer, a performance of a second structure comprising the bone plate and the bone of the first structure, and a second configuration of fixation screws and compression screws securing the bone plate to the bone of the first structure, the second configuration being different than the first configuration; and selecting one of the first and second configurations of fixation screws and compression screws based on the simulations.

26. The method of claim 25, further comprising selecting the selected configuration based at least in part on which configuration produces optimum biomechanics.

27. The method of claim 25, further comprising selecting the selected configuration based at least in part on which configuration produces the best stress distribution for healing the bone.

* * * * *